(12) United States Patent
Vyas

(10) Patent No.: US 6,515,132 B2
(45) Date of Patent: Feb. 4, 2003

(54) PROCESS FOR THE PREPARATION OF ROSIGLITAZONE MALEATE

(75) Inventor: Sharad Kumar Vyas, Ahmedabad (IN)

(73) Assignee: Torrent Pharmaceuticals, Ltd., Abmedabad (IN)

( * ) Notice: Subject to any disclaimer, the term of this patent is extended or adjusted under 35 U.S.C. 154(b) by 0 days.

(21) Appl. No.: 09/951,481

(22) Filed: Sep. 14, 2001

(65) Prior Publication Data

US 2002/0115866 A1 Aug. 22, 2002

(30) Foreign Application Priority Data

Dec. 26, 2000 (IN) ..................................... 714/CAL/2000

(51) Int. Cl.⁷ .................... C07D 417/10; C07D 417/12; A61K 31/4436
(52) U.S. Cl. .................... 546/268.7; 514/342
(58) Field of Search ........................ 546/268.7; 514/342

(56) References Cited

U.S. PATENT DOCUMENTS 5,756,525 A * 5/1998 Hindley et al. .............. 514/272

FOREIGN PATENT DOCUMENTS

| EP | 0306228 A1 | 3/1989 | ......... C07D/277/82 |
|---|---|---|---|
| WO | 94/05659 | 3/1994 | ......... C07D/417/12 |
| WO | WO 01/44240 A1 | 6/2001 | ......... C07D/417/12 |

OTHER PUBLICATIONS

Chemistry a Modern Course, 1975, p. 93, e.g. 26.*
Oxford dictionary of Biochemistry . . . p. 579, definition of room temperature, 1997.*
Li J et al., Improved method for the synthesis of 4–'2–(methyl–2–pyridinylamino) ethoxy 1 benzaldehyde, vol. 134, No. 20, p. 684 May 14, 2001 (Abstract) [XP–00 2187 086].
Cantello B C C et. al, Journal of medicinal chemistry, vol. 37, No. 23, 1994, pp. 3977–3985 [XP–00 2127 002].
Cantello B C C et al., Bioorganic & Medicinal chemistry, vol. 4, No. 10, 1994, pp. 1181–1184 [X P —00 105 2838].
Abarbri M et. AL, Helvetica Chimica Acta, vol. 78, No. 1, Feb. 8, 1995, pp. 109–121[XP–00218 7084].
Reddy K A et. al., Journal of Medicinal Chemistry, vol. 42, No. 17 Aug. 26, 1999, pp. 3265–3278 [XP—00 218 7085].
International Search Report on corresponding PCT application No. PCT/IB 01/01367 Filed on Jul. 30, 2001.
Cantello et al J. Med. Chem 1994, 37, 3977–3985.
Cantello et al Bio–organic & Medicinal Chemistry Letters vol. 4, No. 10 pp. 1181–84.1994.

* cited by examiner

Primary Examiner—Alan L. Rotman
Assistant Examiner—Rita Desai
(74) Attorney, Agent, or Firm—Sughrue Mion, PLLC

(57) ABSTRACT

The invention discloses a process for the preparation of a pyridine derivative namely 5-{4-2(N-methyl-N(2-pyridyl) amino ethoxy]benzyl]thiazolidine-2,4-dione maleate comprising the steps of:

(a) reacting 2-chloropyridine with 2-(N-methyl amino) ethanol;

(b) coupling 2-(N-methyl-N-(2-pyridyl) amino)ethanol) obtained in step (a) and 4-fluorobenzaldehyde in an aprotic polar solvent with an alkali metal hydroxide or an alkali metal alkoxide as base.

(c) isolating the product of the coupling reaction viz 4-[2-(N-methyl-N-(2-pyridyl) amino) ethoxy] benzaldehyde;

(d) converting said isolated benzaldehyde compound of step (c) into 5-[4-[2-N-methyl-N-(2-pyridyl) amino) ethoxy]benzyl]thiazolidine-2,4-dione in a known manner and (e) converting said thiazolidine-2,4-dione compound obtained in step (d) into a pharmaceutically acceptable maleate salt.

10 Claims, No Drawings

PROCESS FOR THE PREPARATION OF ROSIGLITAZONE MALEATE

BACKGROUND OF THE INVENTION

1. Field of the Invention

The present invention relates to a process for the preparation of 5-[4-[2-(N-methyl-N-(2-pyridyl) amino) ethoxy] benzyl]thiazolidine-2,4-dione maleate, namely, rosiglitazone maleate, the antidiabetic compound, which is the preferred drug for non-insulin dependent diabetes mellitus (NIDDM).

2. Description of the Related Art

Diabetes mellitus is a complex, chronically, progressive disease, which can eventually adversely affect the functioning of the kidneys, eyes, nervous and vascular systems. Most individuals diagnosed with diabetes mellitus show symptoms for non insulin dependent diabetes mellitus (NIDDM) that is, Type II diabetes. Type II diabetes is a debilitating disease that arises from improper energy storage and utilization. Type II diabetes is defined by high plasma glucose levels and is characterized by both peripheral insulin resistance and insufficient insulin secretion by the β-cells of the pancreas. The current approach for handling hyperglycemia is to alleviate insulin resistance rather than to stimulate insulin secretion. The thiazolidinedione class of antidiabetics such as pioglitazone, englitazone, troglitazone and ciglitazone have been shown to alleviate insulin resistance in humans.

Rosiglitazone maleate that is 5-[4-[2-(N-methyl-N-(2-pyridyl)amino) ethoxy]benzyl]thiazolidine-2,4-dione maleate of formula (I),

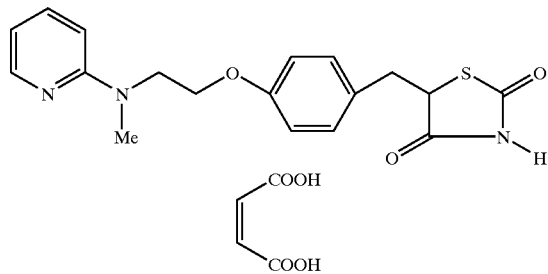

(I)

is a member of thiazolidinedione class and is one of the most potent compounds of this class, with a minimally effective dose of 3 μmol/kg diet. The comparative activity data for the various thiazolidinediones which are all being clinically progressed is summarized below:

| Drug | Minimum effective dose (μmol/kg diet) |
|---|---|
| Rosiglitazone | 3 |
| Pioglitazone | 200 |
| Englitazone | 200 |
| Troglitazone | 600 |
| Ciglitazone | 3000 |

Since, rosiglitazone is the preferred drug for non-insulin dependent diabetes mellitus, hence, the process for its production, yield obtained and costs involved are all constantly being critically surveyed for optimization.

European patent application 0306228, describes the coupling reaction of 2-(N-methyl-N-(2-pyridyl)amino)ethanol with 4-fluorobenzaldehyde in the presence of dimethyl formamide as solvent and sodium hydride as base, but no yield has been reported.

Cantello et. al. (J. Med. Chem. 1994, 37, 3977–3985) have independently prepared rosiglitazone and reported a yield of 48% for the coupling reaction of 2-(N-methyl-N-(2-pyridyl) amino)ethanol with 4-fluorobenzaldehyde in the presence of dimethyl formamide as solvent and sodium hydride as base for the synthesis of 4-[2-(N-methyl-N-(2-pyridyl)amino)ethoxy]benzaldehyde when carried out at a room temperature.

Moreover, Cantello et. al. (Biorganic and Medicinal Chemistry Letters Vol.45, Page 1181–1184, 1994) have reported a yield of 72% when the same reaction was carried out at 80° C.

In the present invention a significantly higher yield of 88%, is obtained in the coupling reaction carried out at room temperature. The reagent used provides a significant increase in yield from 48% to 88% when compared to Cantello's room temperature reaction as also an increase in yield from 72% to 88% when compared to Cantello's reaction at 80° C.

In the final step for the formation of the pharmaceutically acceptable maleate salt, Cantello et. al. have reported a yield of 62% using methanol as solvent. Pool et al (WO94/05659) have disclosed the yield of the crude maleate salt as 87%. In the present invention, a higher yield of 90–95% of the pure maleate salt is obtained using a different solvent.

SUMMARY OF THE INVENTION

The object of the invention is to provide an improved process for the preparation of rosiglitazone maleate in high yield and high grade purity.

A further object of the invention is to provide 4-[2-(N-methyl-N-(2-pyridyl)amino)ethoxy]benzaldehyde in high yield by the coupling reaction of 2-(N-methyl-N-(2-pyridyl) amino)ethanol with 4-fluorobenzaldehyde.

Still another object of the invention is to provide the pharmaceutically acceptable salt, rosiglitazone maleate from rosiglitazone in high yield.

Accordingly, the present invention provides a process for the preparation of 5-[4-[2-(N-methyl-N-(2-pyridyl)amino) ethoxy]benzyl]thiazolidine-2,4-dione maleate, namely, rosiglitazone maleate of formula (I), which comprises the steps of:

a) reacting 2-chloropyridine with 2-(N-methylamino) ethanol to yield the product alcohol 2-(N-methyl-N-(2-pyridyl)amino)ethanol (II);

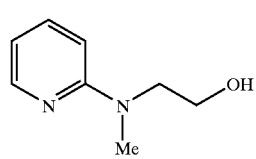

(II)

b) coupling 2-(N-methyl-N-(2-pyridyl)amino)ethanol (II) and 4-fluorobenzaldehyde (III)

(III)

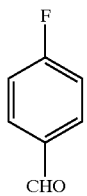

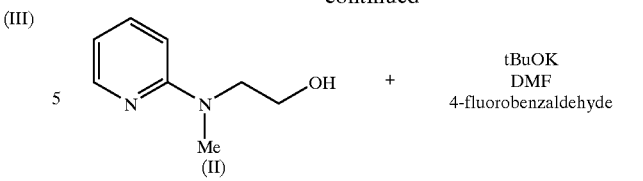

in an aproctic polar solvent with an alkali metal hydroxide or an alkali metal alkoxide as base, at room temperature and preferably at a temperature range of 25° to 30° C.;

c) isolating the product of the coupling reaction, namely 4-[2-(N-methyl-N-(2-pyridyl)amino)ethoxy]benzaldehyde (IV);

(IV)

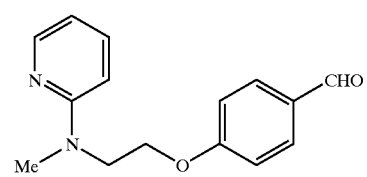

d) converting said compound (IV) into 5-[4-[2-(N-methyl-N-(2-pyridyl)amino)ethoxy]benzyl]thiazolidine-2,4-dione (V) in a manner known per se, and (V)

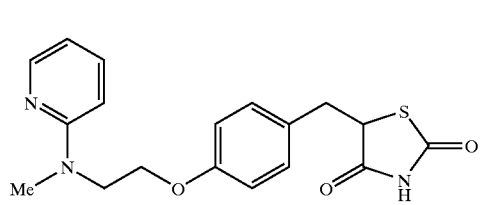

e) converting said compound (V) into its pharmaceutically acceptable maleate salt, 5-[4-[2-(N-methyl-N-(2-pyridyl)amino)ethoxy]benzyl]thiazolidine-2,4-dione maleate (I), by reaction with maleic acid.

DETAILED DESCRIPTION OF THE INVENTION

The synthetic route to the production of rosiglitazone maleate according to the present inventon is shown in the following scheme:

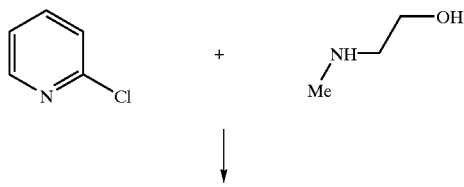

The reaction of 2-chloropyridine with 2-(N-methyl amino)ethanol provides 2-(N-methyl-N-(2-pyridyl)amino)ethanol (II), which on coupling reaction with 4-fluorobenzaldehyde (III) in an aprotic polar solvent with an alkali metal hydroxide or an alkali metal alkoxide as base yields 4-[2-(N-methyl-N-(2-pyridyl)amino)ethoxy]benzaldehyde (IV) with an 88% yield (Reaction I).

Reaction-1

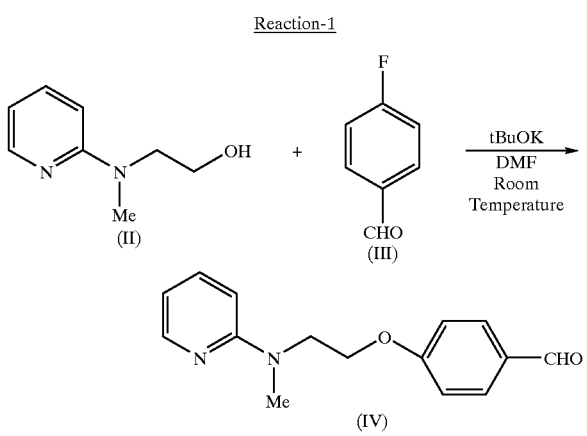

The preferred alkali metal is sodium or potassium and the alkoxide is of a lower alcohol (having $C_1$ to $C_6$) carbon atoms. Preferred alkali metal alkoxide is sodium methoxide and potassium tertiary butoxide and the most preferred alkali metal alkoxide is potassium tertiary butoxide. Further, the preferred alkali metal hydroxide is potassium hydroxide.

The reaction may be carried out in an aprotic polar solvent selected from the group dimethyl sulphoxide, dimethyl formamide and tetrahydrofuran, or mixtures thereof.

4-[2-(N-methyl-N-(2-pyridyl)amino)ethoxy]benzaldehyde (V) was converted into 5-[4-[2-(N-methyl-N-(2-pyridyl)amino)ethoxy]benzyl]thiazolidine-2,4-dione (V), namely, rosiglitazone, in a manner known per se, by Knoevenegal condensation with 2,4-thiazolidinedione, to give the highly crystalline benzylidene derivative (VI), in 95% yield and the subsequent reduction of the double bond with magnesium metal in methanol to obtain rosiglitazone (V) in 72% yield.

In the final step of salt formation, rosiglitazone (V) and maleic acid were refluxed in acetone at 50° to 55° C. to obtain the maleate salt 5-[4-[2-(N-methyl-N-(2-pyridyl)amino)ethoxy]benzyl]thiazolidine-2,4-dione maleate (1), namely rosiglitazone maleate in high yield of 90 to 95% with high grade purity and low moisture content to be effectively dry and free flowing so that it can easily be converted into a pharmaceutical composition.

REACTION-2

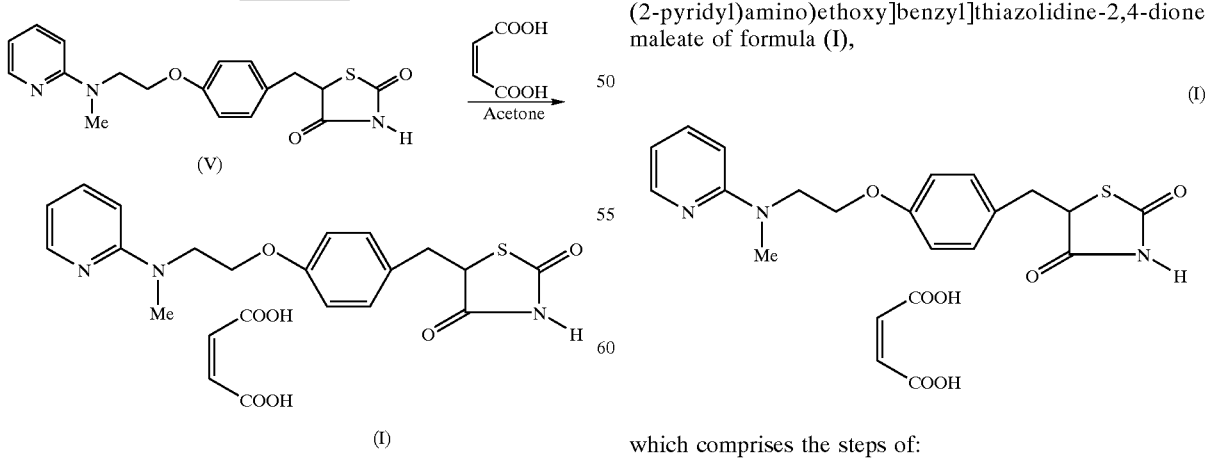

The degree of purity of Rosiglitazone maleate (bulk drug) synthesized according to the instant process is substantially high with the impurity level less than 0.1%. In fact the impurity level is so small that as per current USFDA Standard and other international regulations, no further analysis of the impurity is required. This level of purity has been possible to achieve by following the process steps according to the instant invention.

Acetone can also be easily and effectively removed compared to the alcoholic solvent methanol which was used in prior art process.

The following procedures and examples illustrate the invention but do not limit it in anyway.

EXAMPLE

Preparation of 4-[2-(N-Methyl-N-(2-pyridyl)amino)ethoxy]benzaldehyde (IV):

In a 2l three necked, round bottom flask, 500 ml dimethylformamide is added, followed by addition of 100 g of 2-(N-methyl-N-(2-pyridyl)amino)ethanol (II) and 100 g of 4-fluorobenzaldehyde (III) was added to the reaction mixture and it was stirred for 10 minutes at room temperature and 80 g of potassium tertiary butoxide was added to the reaction mixture. The reaction was monitored by TLC. After completion of the reaction, the reaction mixture was cooled to 5–10° C. and under the cold conditions, 1.5 l of water was added and stirred for 15 min. The mixture was extracted with 4×500 ml of ethyl acetate. The combined organic layer was washed with 3×1 l water. The organic layer was dried over anhydrous sodium sulphate and concentrated under reduced pressure to give 148 g (88%) of 4-[2-(N-methyl-N-(2-pyridyl)amino)ethoxy)benzaldehyde (IV).

Preparation of 5-14-[2-(N-Methyl-N-(2-pyridyl)amino)ethoxy]benzyl]thiazolidine-2,4-dione Maleate (I):

800 g of 5-[4-[2-(N-methyl-N-(2-pyridyl)amino)ethoxy]benzyl]thiazolidine-2,4-dione (V) and 280 mg maleic acid were dissolved in 1.3 l of acetone in 5 l three necked round bottom flask. The reaction mixture was heated to 50°–55° C. and the solution was filtered and slowly cooled to obtain 986 g of 5-[4-[2-(N-methyl-N-(2-pyridyl)amino)ethoxy]benzyl]thiazolidine-2,4-dione maleate (1) (yield 95%; mp 120–122° C.).

What is claimed is:
1. A process for the preparation of 5-[4-[2-(N-methyl-N-(2-pyridyl)amino)ethoxy]benzyl]thiazolidine-2,4-dione maleate of formula (I),

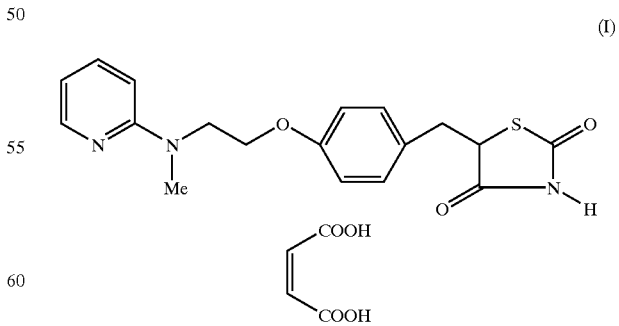

which comprises the steps of:
 a) reacting 2-chloropyridine with 2-(N-methyl amino ethanol to yield the product alcohol 2-(N-methyl-N-(2-pyridyl)amino)ethanol (II);

(II)

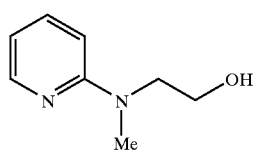

b) coupling 2-(N-methyl-N-(2-pyridyl)amino)ethanol (II) and 4-fluorobenzaldehyde (III)

(III)

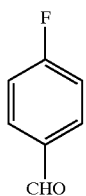

in an aprotic polar solvent with an alkali metal hydroxide or an alkali metal alkoxide as base at room temperature;

c) isolating the product of the coupling reaction, 4-[2-(N-methyl-N-(2-pyridyl)amino)ethoxy]benzaldehyde (IV);

(IV)

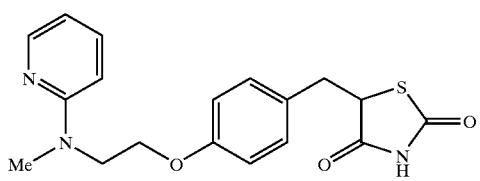

d) converting said compound (IV) into 5-[4-[2-(N-methyl-N-(2-pyridyl)amino)ethoxy]benzyl]thiazolidine-2,4-dione (V); and (V)

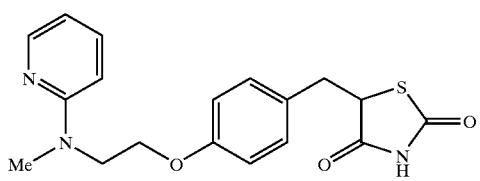

e) converting compound (V) into its pharmaceutically acceptable maleate salt, 5-[4-[2-(N-methyl-N-(2-pyridyl)amino)ethoxy]benzyl]thiazolidine-2,4-dione maleate (I), by reaction with maleic acid.

2. A process as claimed in claim 1, wherein said alkali metal is sodium or potassium.

3. A process as claimed in claim 1, wherein said alkoxide is of a lower alcohol having $C_1$ to $C_6$ carbon atoms.

4. A process as claimed in claim 1, wherein said alkali metal alkoxide is selected from amongst sodium methoxide and potassium tertiary butoxide.

5. A process as claimed in claim 4, wherein said alkali metal alkoxide is potassium tertiary butoxide.

6. A process as claimed in claim 1, wherein said alkali metal hydroxide is potassium hydroxide.

7. A process as claimed in claim 1, wherein said conversion step (e) is carried out in acetone as a solvent.

8. A process as claimed in claim 1, wherein step (e) is carried out at a temperature of 50 to 55° C.

9. A process as claimed in claim 1, which comprises conducting coupling step (b) at a temperature range of 250 to 30° C.

10. A process as claimed in claim 1, wherein said converting step (d) comprises Knoevenegal condensation with 2,4-thiazolidinedione.

* * * * *